(12) United States Patent
Xiao et al.

(10) Patent No.: US 10,139,385 B2
(45) Date of Patent: Nov. 27, 2018

(54) METHOD OF TRACING CHEMICAL QUANTITIES USING ENCAPSULATED FLUORESCENT DYES

(71) Applicant: Ecolab USA Inc., Naperville, IL (US)

(72) Inventors: Lan Xiao, Naperville, IL (US); Yanjiao Xie, Forest Park, IL (US)

(73) Assignee: Ecolab USA Inc., Naperville, IL (US)

( * ) Notice: Subject to any disclaimer, the term of this patent is extended or adjusted under 35 U.S.C. 154(b) by 156 days.

(21) Appl. No.: 13/964,478

(22) Filed: Aug. 12, 2013

(65) Prior Publication Data

US 2015/0041406 A1 Feb. 12, 2015

(51) Int. Cl.
*G01N 33/18* (2006.01)
*C02F 1/52* (2006.01)
*G01N 21/64* (2006.01)
*C02F 1/50* (2006.01)
*C02F 1/54* (2006.01)
*C02F 1/56* (2006.01)
*C02F 5/00* (2006.01)
*C12Q 3/00* (2006.01)
*C02F 103/02* (2006.01)
*C02F 103/10* (2006.01)
*C02F 103/28* (2006.01)
*C02F 103/36* (2006.01)

(52) U.S. Cl.
CPC .............. *G01N 33/18* (2013.01); *C02F 1/52* (2013.01); *C02F 1/5209* (2013.01); *G01N 21/643* (2013.01); *C02F 1/50* (2013.01); *C02F 1/5236* (2013.01); *C02F 1/54* (2013.01); *C02F 1/56* (2013.01); *C02F 5/00* (2013.01); *C02F 2103/023* (2013.01); *C02F 2103/10* (2013.01); *C02F 2103/28* (2013.01); *C02F 2103/365* (2013.01); *C02F 2303/08* (2013.01); *C02F 2305/00* (2013.01); *C02F 2305/04* (2013.01); *C12Q 3/00* (2013.01); *G01N 2021/6439* (2013.01)

(58) Field of Classification Search
CPC .. C02F 1/52; C02F 1/5209; C02F 1/50; C02F 1/5236; C02F 1/54; C02F 1/56; C02F 5/00; C02F 2305/00; C02F 2305/04; C02F 2303/08; C02F 2103/023; C02F 2103/10; C02F 2103/28; C02F 2103/365; G01N 33/18; G01N 21/643; G01N 2021/6439

See application file for complete search history.

(56) References Cited

U.S. PATENT DOCUMENTS

| | | | |
|---|---|---|---|
| 3,518,205 A * | 6/1970 | Vukasovich | ............. 252/301.21 |
| 4,647,675 A | 3/1987 | Mayer et al. | |
| 4,783,314 A | 11/1988 | Hoots et al. | |
| 4,992,380 A | 2/1991 | Moriarty et al. | |
| 5,171,450 A | 12/1992 | Hoots | |
| 5,354,692 A | 10/1994 | Yang et al. | |
| 5,435,969 A * | 7/1995 | Hoots | ................... G01N 21/643 422/14 |
| 5,705,394 A * | 1/1998 | Ananthasubramanian | ................... G01N 21/6428 422/16 |
| 5,808,103 A | 9/1998 | Ward et al. | |
| 6,248,596 B1 | 6/2001 | Durst et al. | |
| 6,685,840 B2 * | 2/2004 | Hatch | ............ 210/739 |
| 7,220,382 B2 | 5/2007 | Godfrey et al. | |
| 8,088,629 B1 * | 1/2012 | Lugade et al. | ................ 436/174 |
| 2002/0155089 A1 | 10/2002 | Chowdhary et al. | |
| 2004/0139565 A1 * | 7/2004 | Banerjee | .................. C08J 3/215 8/509 |
| 2005/0025659 A1 | 2/2005 | Godfrey et al. | |
| 2005/0121814 A1 * | 6/2005 | Morrison | .................. B01J 13/04 264/4.1 |
| 2006/0160227 A1 * | 7/2006 | Sethumadhavan et al. | .... 436/56 |
| 2007/0117215 A1 * | 5/2007 | Davis | ................... G01N 21/643 436/172 |
| 2008/0305157 A1 * | 12/2008 | English | ................ A61K 9/1272 424/450 |
| 2009/0260767 A1 | 10/2009 | Gerli et al. | |
| 2010/0012284 A1 | 1/2010 | Kaub | |
| 2010/0330366 A1 | 12/2010 | Keiser et al. | |
| 2013/0078730 A1 | 3/2013 | Murcia et al. | |
| 2016/0041135 A1 * | 2/2016 | Lannutti | ............ G01N 21/6408 435/29 |

FOREIGN PATENT DOCUMENTS

JP 401038195 * 2/1989
WO WO 2010/140032 A2 12/2010

OTHER PUBLICATIONS

Solkolv et al. Self Assembly of ultra-bright fluorescent silica particles, small, 2007, 3, No. 3, 419-423.*
Jyothi et al., Microencapsulation : A Review, International Journal of Pharma and Bio Sciences, vol. 3, Issue 1, Mar. 2012, pp. 509-531.*
Jeon et al., Microviscosity in PEO-PPo-PEO Block Copolymers Probed by Fluorescence Depolarizartion kinetics, Journal of Polymer Science: Part B Polymer Physics, vol. 40, 2883-2888, 2002.*
Jyothi Sri.S, et al., Microencapsulation: A Review, International Journal of Pharma and Bio Sciences, Jan.-Mar. 2012, vol. 3, Issue 1, Department of Pharmaceutics, Hindu College of Pharmacy, Guntur, India.
European Patent Office, Extended European Search Report in European Patent Application No. 14836331.0, dated Feb. 14, 2017, 7 pp.
Vogel et al., "Dimer-to-monomer transformation of Rhodamine 6G in aqueous PEO-PPO-PEO block copolymer solutions," *Macromolecules*, 35.6, 2002, pp. 2063-2070.

* cited by examiner

*Primary Examiner* — Amina S Khan (74) *Attorney, Agent, or Firm* — Leydig, Voit & Mayer, Ltd.

(57) ABSTRACT

The invention provides methods and compositions for utilizing encapsulated tracer dyes in difficult liquids such as wastewater or with highly reactive treatment chemicals such as aluminum-based coagulants. In difficult liquids or highly reactive treatment chemicals even so-called "inert" tracers end up reacting and their fluorescence changes. As a result they are inconsistent and cannot be used to measure the amount of treatment chemical present. But by encapsulating the tracer dyes, even non inert tracer dyes become inert and they can reliably be used to measure the amount of treatment chemical present even if highly reactive or in a difficult liquid.

17 Claims, 10 Drawing Sheets

METHOD OF TRACING CHEMICAL QUANTITIES USING ENCAPSULATED FLUORESCENT DYES

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The invention relates to compositions, methods, and apparatuses for measuring chemical dosages. In particular the invention encompasses fluorescently tracing treatment chemicals that are added to industrial wastewater. The invention allows for the efficient treatment of industrial wastewater using a treatment technology such as TRASAR® technology or 3D TRASAR® technology, each available from Nalco, an Ecolab Company, 1601 West Diehl Road, Naperville, Ill. 60563.

BACKGROUND OF THE INVENTION

Wastewater, particularly industrial wastewater, can be difficult to cost-effectively treat because of its physical and chemical properties. Wastewater can be comprised of various chemical and biological species, including suspended solids. As such, there has been a long-felt but unmet need to more efficiently treat wastewater, particularly industrial wastewater.

The use of dyes as tracing chemicals was patented by John Hoots of Nalco Company in 1988 (U.S. Pat. No. 4,783,314), and subsequent patent applications were filed for specific industrial applications, such as disulfonated anthracenes as inert tracer for boiler water (U.S. Pat. No. 7,220,382).

The synthesis of rhodamine dyes is described in U.S. Pat. No. 4,647,675. As a commercially available dye, Rhodamine WT has been used in hydrological studies of surface water, ground water, and wastewater (*Dyes As Hydrological Tracers*, by Mon, J. and Flury M, Water Encyclopedia, 95-102; YSI Environmental 1006 E46-01) (2005); and *Herbicide tracing in surface water and ground water* (YSI Environmental 1006 E46-01).

Industrial wastewater treatment processes have not been able to use fluorescent tracers due to its high fluorescence background and high interfering light-scattering signal from suspended solids. It is very difficult to find an inert dye that overcomes the interference from high fluorescent background and high suspended solids present in industrial wastewater. The interference from charged coagulants and flocculants and other contaminants in wastewater add difficulty in finding a suitable inert fluorescent dye.

Accordingly, there is a need for and clear utility in a fluorescent dye that can be used in tracing treatment chemicals in industrial wastewater. Desirably, the dye will overcome the obstacles presented by industrial wastewater that make it difficult to fluorescently trace treatment chemicals.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR § 1.56(a) exists.

BRIEF SUMMARY OF THE INVENTION

To satisfy the long-felt but unsolved needs identified above, at least one embodiment of the invention is directed towards a method of dosing a treatment chemical with a tracer dye wherein the dye is encapsulated. The dye may be introduced into a process system, wherein the spectrometry properties of the encapsulated dye are not substantially altered by the materials in process system or by being co-present with the treatment chemical. The encapsulated dye may be either pre-mixed with the treatment chemical or mixed with the treatment chemical as they are added to a process system.

The method may further comprise calculating the amount of treatment chemical within the process system by measuring spectrometry properties of the encapsulated dye and correlating that measurement with an amount of treatment chemical predetermined to be associated with the measured spectrometry properties. The tracer dyes may have fluorescent emission wavelength higher than 550 nm. The dye may be selected from the list of derivatives of xanthene, oxazine, cyanine, styryl, coumarin, porphin, nanocrystal, perylene, phthalocyanine, and any combinations thereof. The dye may be xanthene derivatives such as but not limited to rhodamine WT, sulforhodamine B, rhodamine B and any combinations thereof. The treatment chemical may be one selected from coagulants, flocculants, anti-scaling agents, anti-corrosion agents, biocide, oxygen scavengers, hardness removal agents, and any combination thereof. The treatment chemical may be inorganic, organic and/or a blend of inorganic and organic materials. The treatment chemical may be inorganic coagulant or blend of inorganic and organic coagulants containing aluminum or iron salt.

The method may further comprise the steps of encapsulating dye by mixing a dye with a surfactant with proper HLB in water solution. The surfactant may be one selecting from cationic, anionic, amphoteric, non-ionic and zwitterionic. The surfactant may be is a PEO-PPO-PEO tri-block copolymer. The treatment chemical may be a tagged polymer.

The ratio of dye to treatment chemical may be from 1:100 to 100:1 and may also be 1:25 to 25:1, 1:10 to 10:1, and/or 1:10 to 2:1. The method may further comprise the step of encapsulating the dye by mixing dry tracer dye with a melted form of dry treatment chemical to form a melted mixture, cooling the melted mixture to form a solid mass, and dissolving the melted mass within water. The method may further comprise the step of encapsulating the dye by dissolving the treatment chemical in water to form a solution, and then dissolve the dye in the solution. The process may be one selecting from water in: a wastewater treatment system, a boiler, a cooling tower, a raw water treatment system, a membrane treatment system, a pulp and paper industry process, a food and beverage industry, a manufacturing industry, and a petroleum or petrochemical refinery industry.

Additional features and advantages are described herein, and will be apparent from, the following Detailed Description.

BRIEF DESCRIPTION OF THE DRAWINGS

A detailed description of the invention is hereafter described with specific reference being made to the drawings in which.

For the purposes of this disclosure, like reference numerals in the figures shall refer to like features, and like measurements shall be indicative of the same principles unless otherwise indicated. The drawings are only an exemplification of the principles of the invention and are not intended to limit the invention to the particular embodiments illustrated.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

The following definitions are provided to determine how terms used in this application, and in particular how the claims, are to be construed. The organization of the definitions is for convenience only and is not intended to limit any of the definitions to any particular category.

"Consisting Essentially of" means that the methods and compositions may include additional steps, components, ingredients or the like, but only if the additional steps, components and/or ingredients do not materially alter the basic and novel characteristics of the claimed methods and compositions.

"Encapsulation" means positioning a mass of a composition of matter (which may be a spectrometry active material (including but not limited to fluorescent material)) within the core of a capsule, the core is surrounded by a shell capsule, the encapsulated material may be so contained by the shell that the core or the spectrometry active material may avoid any direct contact with the liquid the capsule is within or with a chemical fed into the liquid alongside the capsule, or the capsule may limit the number or type of interactions between the core and other materials such that the core is substantially inert or at least less reactive than it would be if not so encapsulated, the capsule may have an HLB such that when at equilibrium substantially all of the encapsulated material remains within the capsule and substantially no material which substantially alter would a spectrometric or physical property of the encapsulated material comes into contact with it, or the encapsulation may reduce such exiting of the core that the core material is substantially inert, the capsule may be of mononuclear, polynuclear, and/or matrix type morphology, capsules include micelles, microcapsules, and nanocapsules, and may range in diameter from 1 meter or larger to 0.0001 nm or smaller, cores may range in diameter from 0.5 meter or larger to 0.00001 nm or smaller.

"Coagulant" is a water treatment chemical often used in solid-liquid separation stage to neutralize charges of suspended solids/particles so that they can agglomerate, coagulants are often categorized as inorganic coagulants, organic coagulants, and blends of inorganic and organic coagulants, inorganic coagulants often include or comprise aluminum or iron salts, such as aluminum sulfate/chloride, ferric chloride/sulfate, polyaluminum chloride, and/or aluminum chloride hydrate, organic coagulants are often positively charged polymeric compounds with low molecular weight, including but not limited to polyamines, polyquaternaries, polyDADMAC, Epi-DMA, additional properties and examples of coagulants are recited in *Kirk-Othmer Encyclopedia of Chemical Technology*, 5th Edition, (2005), (Published by Wiley, John & Sons, Inc.).

"Flocculant" means a composition of matter which when added to a liquid carrier phase within which certain particles are thermodynamically inclined to disperse, induces agglomerations of those particles to form as a result of weak physical forces such as surface tension and adsorption, flocculation often involves the formation of discrete globules of particles aggregated together with films of liquid carrier interposed between the aggregated globules, as used herein flocculation includes those descriptions recited in ASTME 20-85 as well as those recited in Kirk-Othmer Encyclopedia of Chemical Technology, 5th Edition, (2005), (Published by Wiley, John & Sons, Inc.).

"HLB" means the hydrophillic-lipophillic balance of a material which is a measure of the degree to which it is hydrophilic or lipophilic, it can be determined by the equation:

$$HLB = 20 * Mh/M$$

in which Mh is the molecular mass of the hydrophilic portion of the Molecule, and M is the molecular mass of the whole molecule, giving a result on a scale of 0 to 20. An HLB value of 0 corresponds to a completely lipidphilic/hydrophobic material, and a value of 20 corresponds to a completely hydrophilic/lypidphobic material. HLB values are commonly characterized as:
HLB<10: Lipid soluble (water insoluble)
HLB>10: Water soluble (lipid insoluble)
HLB from 4 to 8 indicates an anti-foaming agent
HLB from 7 to 11 indicates a W/O (water in oil) emulsifier HLB from 12 to 16 indicates O/W (oil in water) emulsifier
HLB from 11 to 14 indicates a wetting agent
HLB from 12 to 15 indicates a detergent
HLB of 16 to 20 indicates a solubiliser or hydrotrope.

"Spectrometry" and "Spectroscopy" means the process of analyzing the interaction between a sample of matter and electromagnetic radiation to determine one or more physical properties of the sample of matter. Forms of electromagnetic radiation used include but are not limited to one or more of microwave, terawave, infrared, near infrared, visible, ultraviolet, x-ray, radiation. The analysis includes measurements of one or more of the radiation's absorption, emission, fluorescence, colorometrics, color changes, reflection, scattering, impedance, refraction, and resonance by the sample of matter.

"Surfactant" is a broad term which includes anionic, nonionic, cationic, and zwitterionic surfactants. Enabling descriptions of surfactants are stated in *Kirk-Othmer, Encyclopedia of Chemical Technology*, Third Edition, volume 8, pages 900-912, and in *McCutcheon's Emulsifiers and Detergents*, both of which are incorporated herein by reference.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the Kirk-Othmer Encyclopedia of Chemical Technology, 5th Edition, (2005), (Published by Wiley, John & Sons, Inc.) this definition shall control how the term is to be defined in the claims.

At least one embodiment of the invention is directed towards adding an encapsulated fluorescent material (a tracer dye) to a treatment chemical in a dosage such that the amount of treatment chemical added to a system can be determined from the fluorescence of the fluorescent material.

In at least one embodiment the tracer dye and/or the method of its introduction to a chemical and/or the process system it is used within is one or more of those described in: U.S. patent application Ser. Nos. 13/416,272 and 13/730,087, US Published Patent Application 2005/0025659, and/or U.S. Pat. Nos. 4,783,314, 4,992,380; and 5,171,450. As described therein inert tracer dyes are dosed within treatment chemicals that are added to industrial processes. The tracer dyes are either pre-mixed with the chemical or mixed with the chemical as they are added to a process system. The treatment chemical addresses some need in the system including but not limited to coagulating waste materials in wastewater, mitigating corrosion, and reducing scale. The inert tracer is dosed in an amount such that a measurement of its fluorescence indicates amount of the treatment chemical which has been added to the system.

A key requirement of such a method however requires that the tracer in fact be inert and not interact with either background materials present in the industrial process and/or treatment chemicals added to the system. If not inert, an interaction may result in a variation in the fluorescence of the not so-inert tracer which would result in a false measurement of the amount of chemical added.

Figure 3:
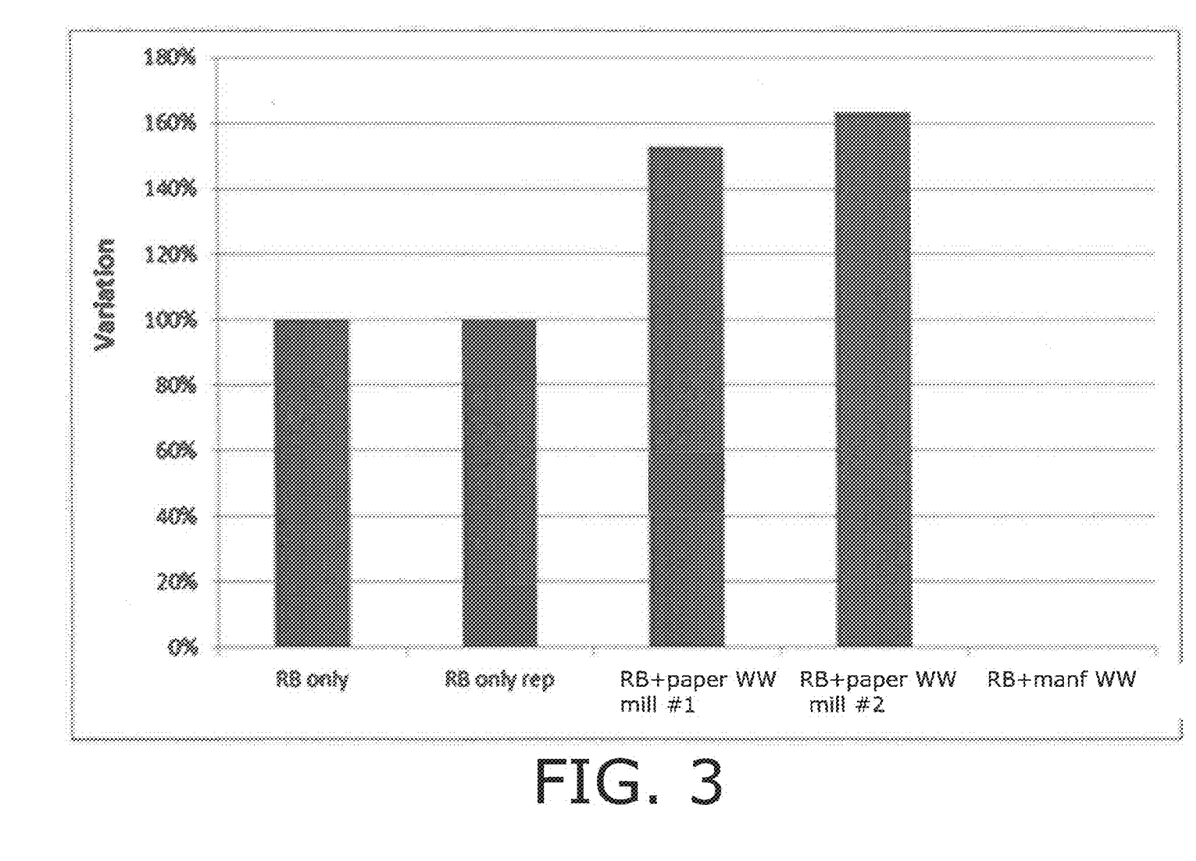
FIG. 3 is a graph illustrating RB dye's fluorescence variations when placed in wastewaters from different industries.
Figure 4:
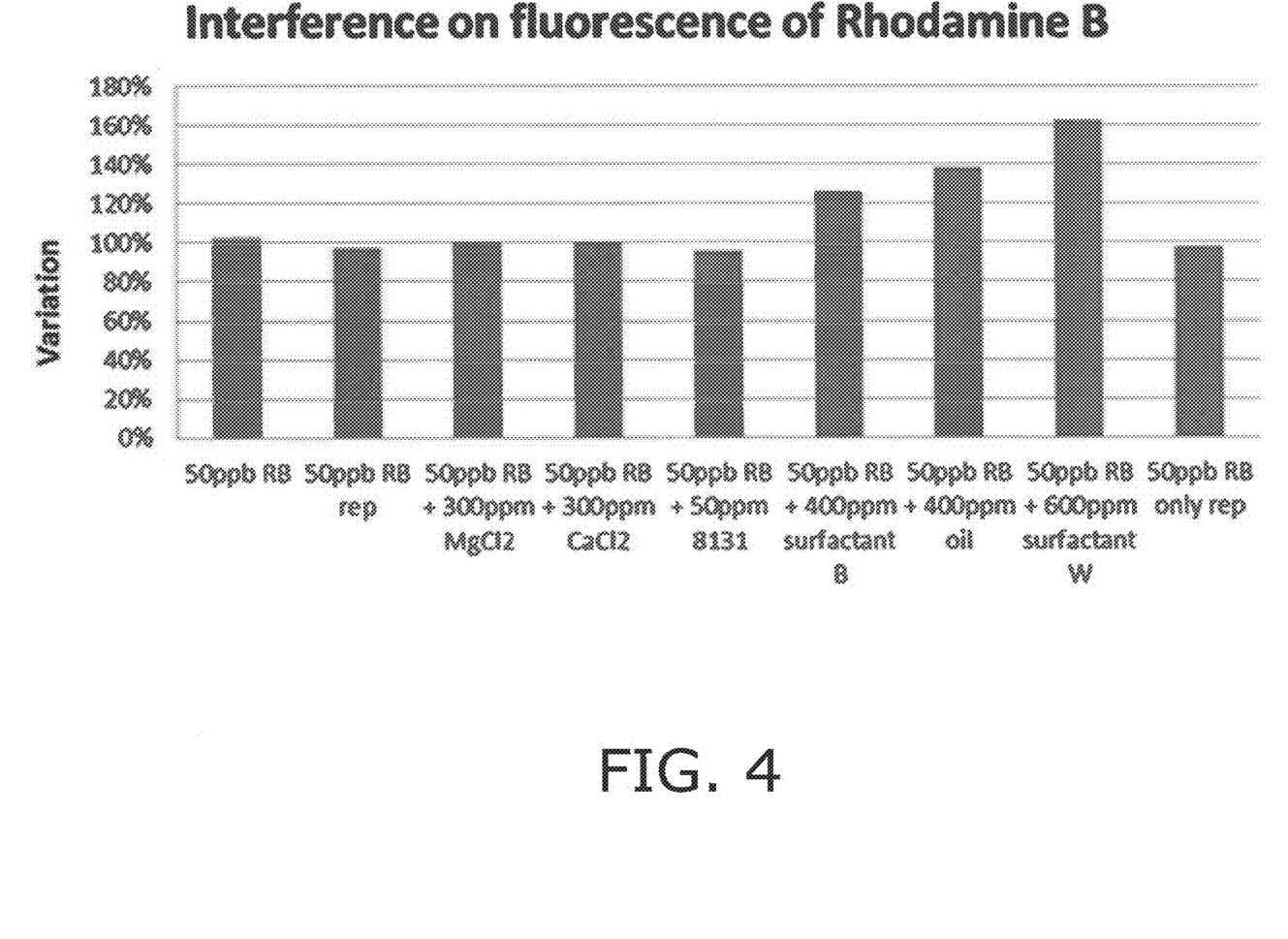
FIG. 4 is a graph illustrating RB dye's fluorescence variations when in contact with different kinds of wastewater contaminants.
Figure 6:
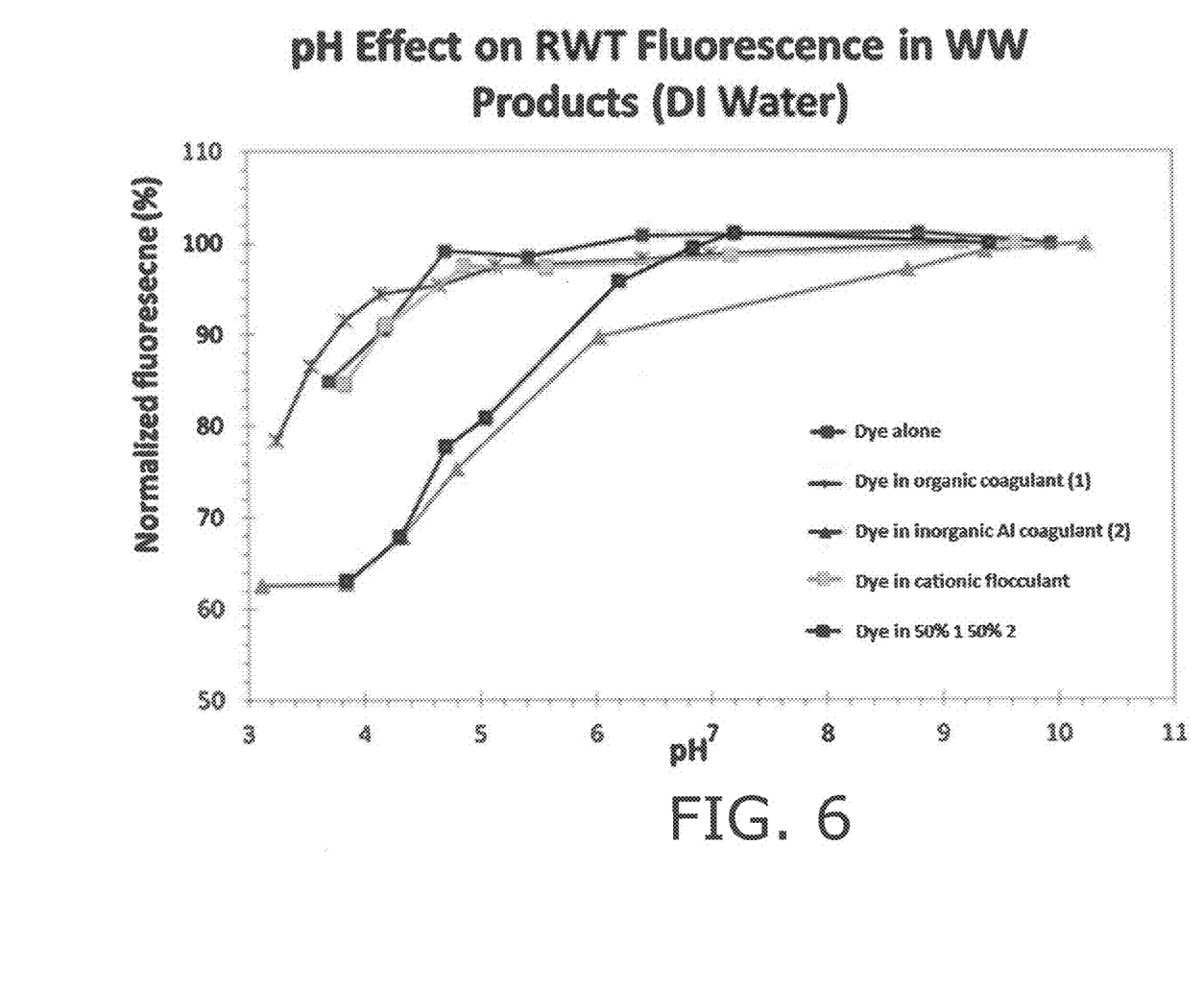
FIG. 6 is a graph illustrating RWT dye alongside a wastewater treatment chemical displays fluorescence variations at different pHs.

Unfortunately many tracer dyes are not as inert as desired when in contact with certain chemicals added to an industrial process. This is particularly the case with regards to ionic chemicals with a high positive charge (+2 per atom or higher) such as but not limited to inorganic coagulants and/or aluminum containing chemicals. In addition in many process systems are "difficult liquids", they contain materials (such as but not limited to contaminants) which are highly reactive with fluorescent material. Also pH and temperature conditions alter the extent to which such interactions occur. As a result many would be tracers cannot be used because they interact with the chemical or with materials within the system. An example of this is the use of Rhodamine B (RB) in wastewater, as illustrated in FIG. 3 & FIG. 4. The fluorescence of RB varied in wide range when in contact with different kinds of wastewater (FIG. 3) or when in the presence of different kinds of wastewater contaminants (FIG. 4). Another example of this is the use of Rhodamine WT (RWT). It displays wide variation of fluorescence when in contact with inorganic and inorganic/organic blend coagulants at pH below 6 as illustrated in FIG. 6. In at least one embodiment an encapsulated tracer dye is used to address these problems.

In the context of wastewater systems treated with inorganic coagulants the need for an effective inert tracer dye is particularly acute. A highly effective class of treatment chemicals commonly used to treat wastewater are coagulants, especially inorganic coagulants such as but not limited to aluminum or ion based coagulants. Unfortunately many tracer materials used in other process systems are not truly inert when in the presence of inorganic coagulants and/or aluminum/ion based coagulants. An example of this is the use of Sulforhodamine (SRB) with treatment chemicals such as inorganic, organic coagulants or flocculants. Sulforhodamine displays wide variation when in contact with coagulants or flocculants, as illustrate in FIG. 5.

Figure 7:
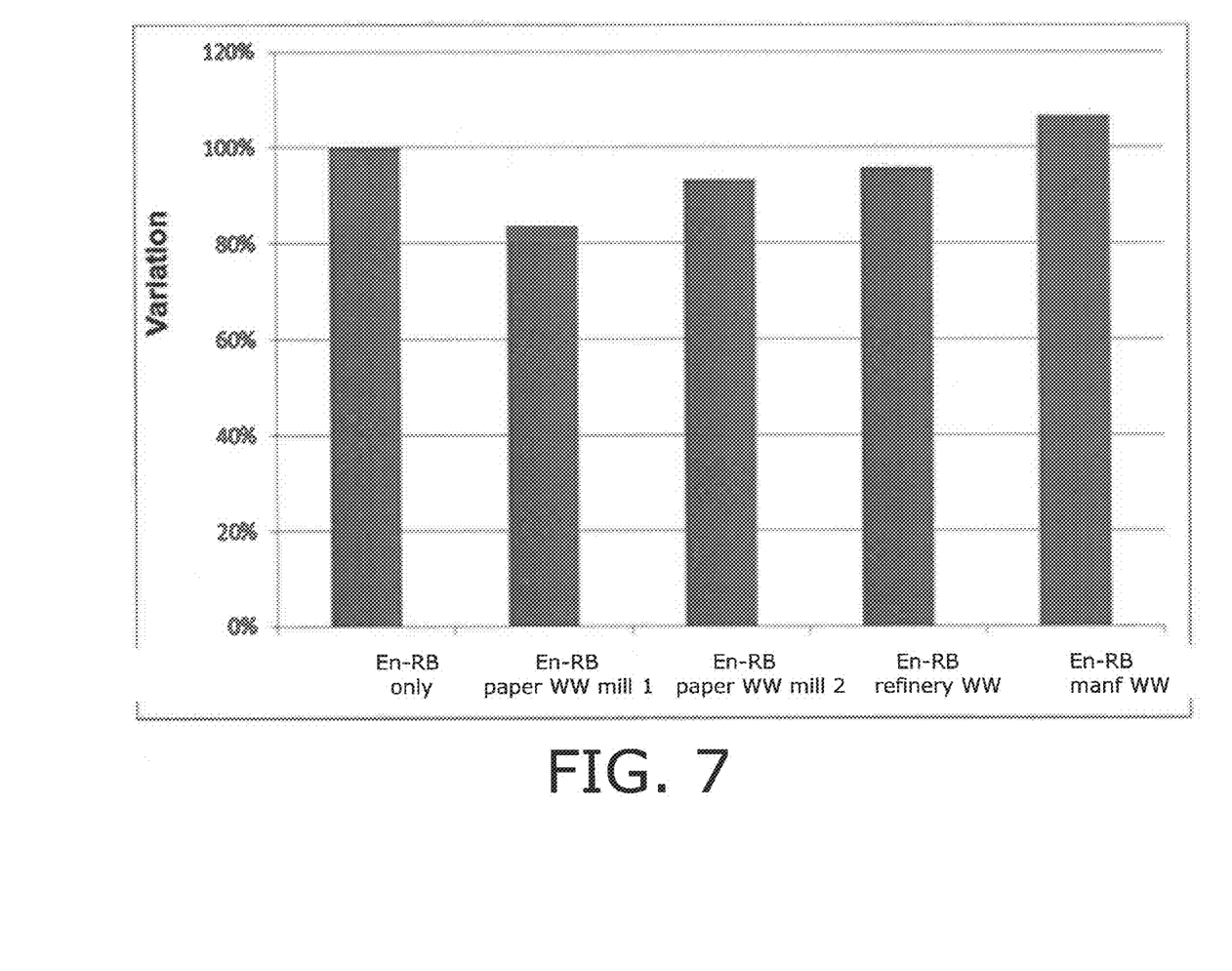
FIG. 7 is a graph illustrating that the inventive dye displays constant fluorescence in the presence of wastewaters from different industries.
Figure 8:
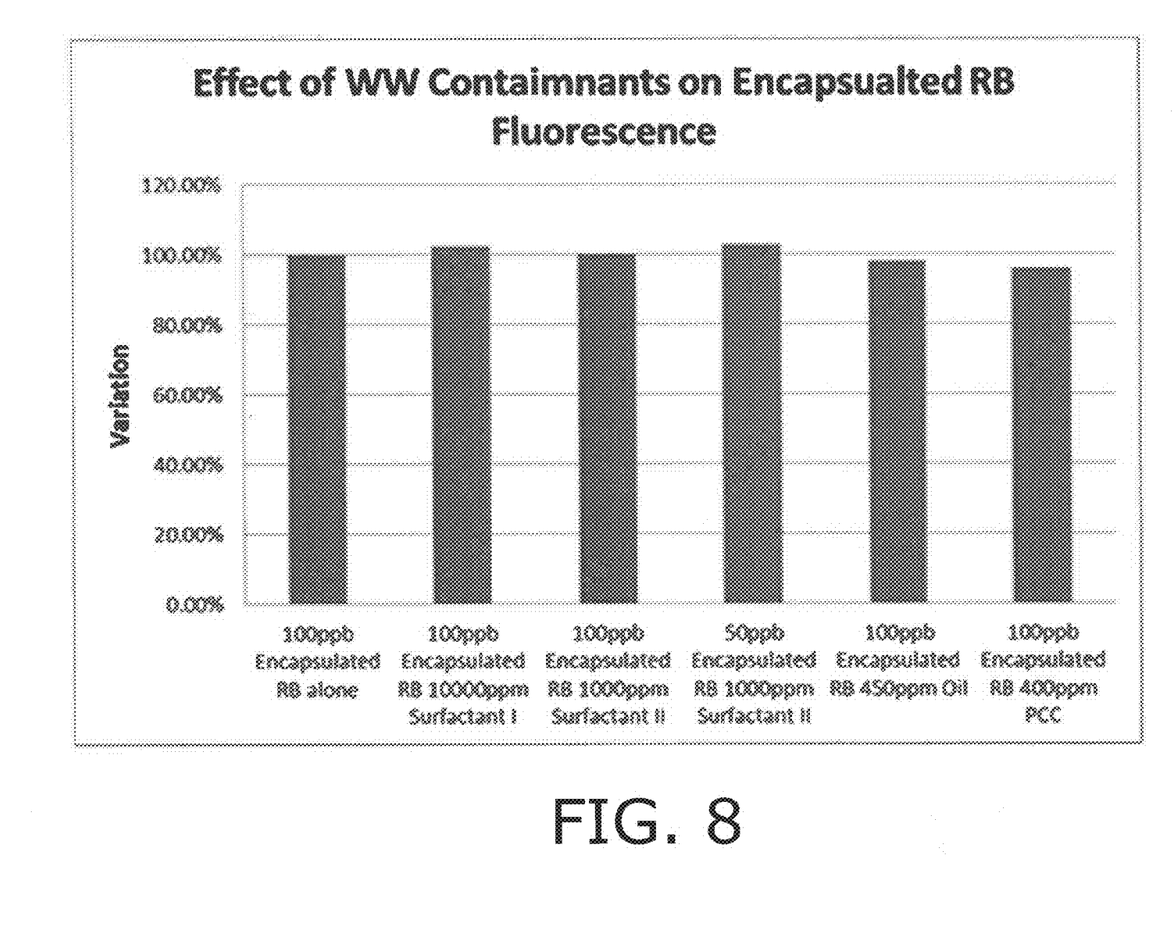
FIG. 8 is a graph illustrating that the invention displays constant fluorescence in the presence of different kinds of wastewater contaminants.
Figure 9:
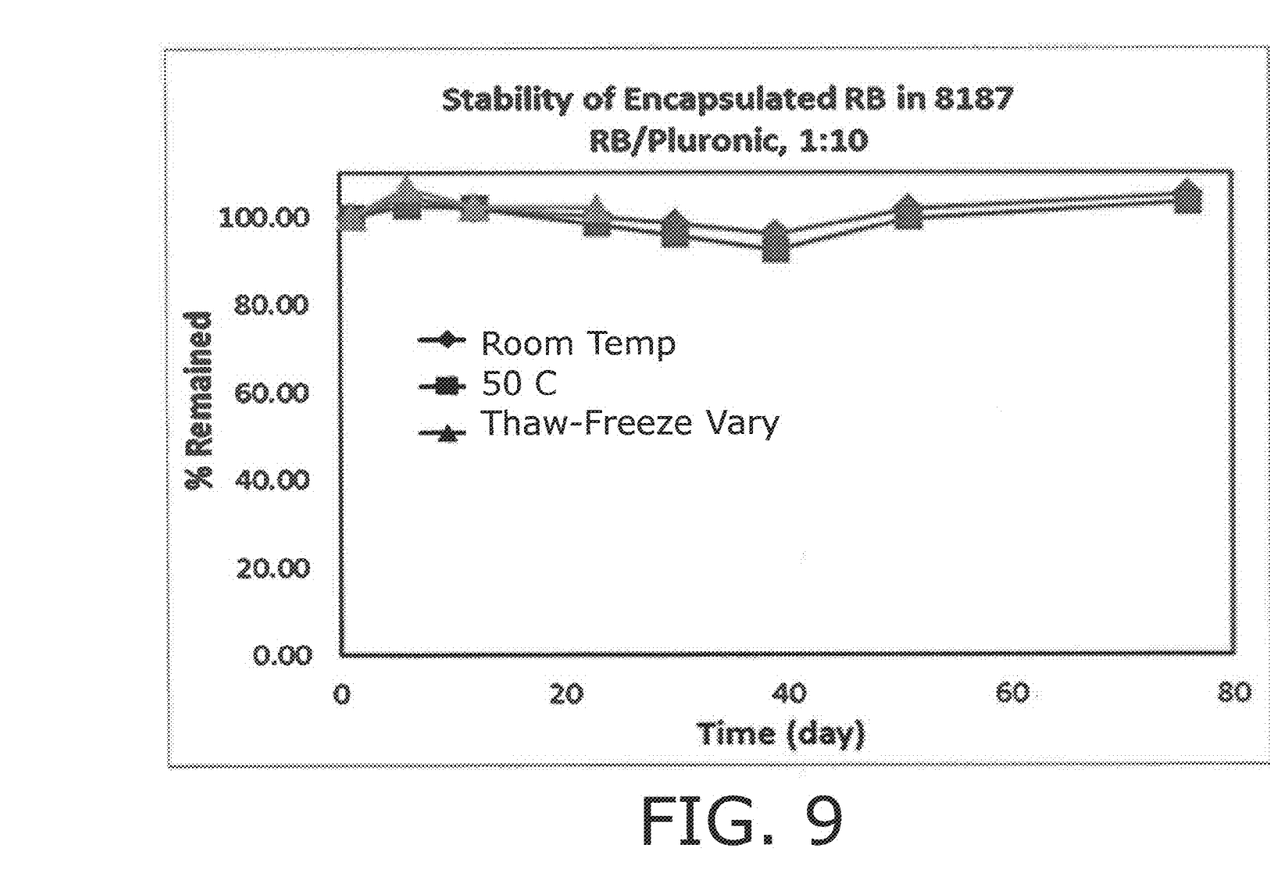
FIG. 9 is a graph illustrating the stability of the invention at room temperature, at 50° C., and in an environment alternating between freezing and thawing.

Fortunately encapsulation of the tracer materials prevents unwanted interactions between the tracer material and the treatment chemical, and between the tracer material and materials present in the system while preserving fluorescence properties. In at least one embodiment the encapsulation, allows for the use of a tracer in a system that would otherwise interact with and have a variation in fluorescence. An example of this is the use of Rhodamine B in wastewater. As illustrated in FIGS. 3 and 4, Rhodamine B displays wide fluorescence variation when in contact with different kinds of wastewater or when in the presence of different kinds of wastewater contaminants. However, as illustrated in FIGS. 7 and 8, when Rhodamine B is in encapsulated it does not have this variation in fluorescence and therefore a reliable tracer dye.

Figure 10:
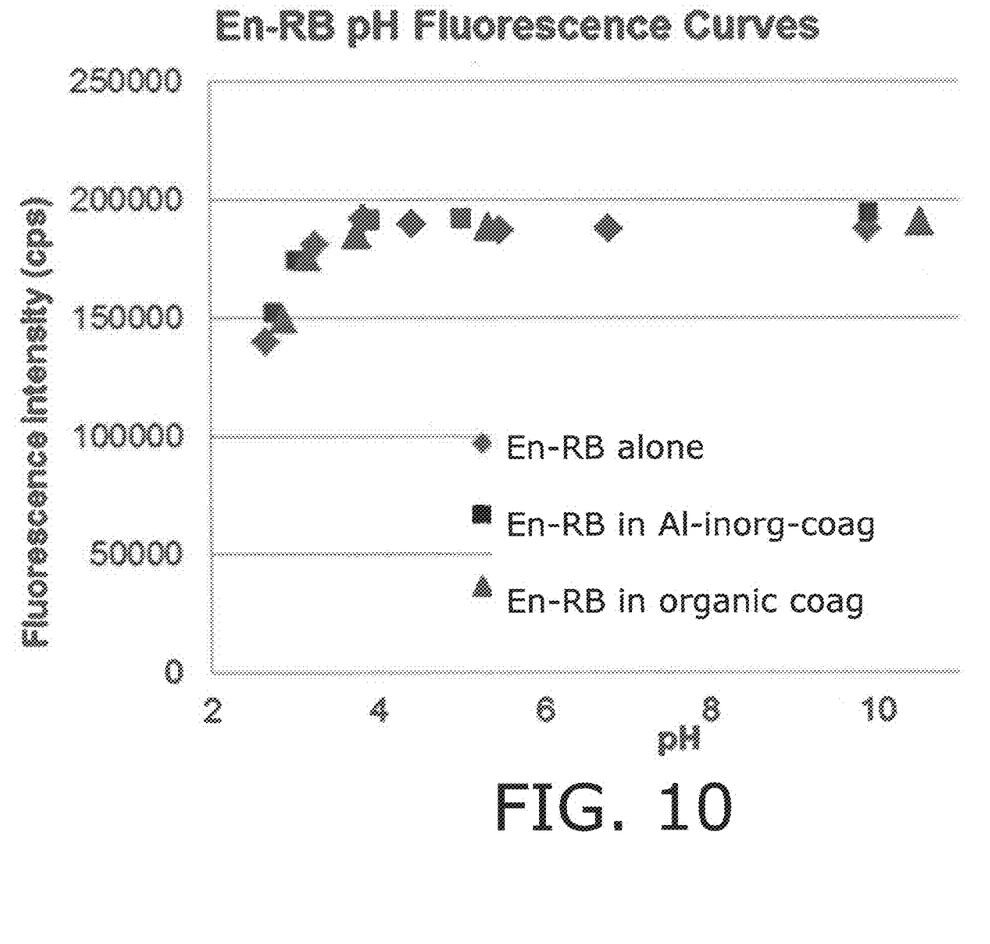
FIG. 10 is a graph illustrating the constant fluorescence of the invention when applied alongside various chemical additives or alone at different pHs.

In at least one embodiment the encapsulation, allows for the use of a tracer in the company of a treatment chemical that would otherwise react with and have a variation in fluorescence. An example of this is the use of Sulforhodamine with treatment chemicals such as inorganic coagulants or inorganic flocculants. Sulforhodamine displays wide variation when in contact with inorganic coagulants or inorganic flocculants. However when Sulforhodamine is in encapsulated it does not have this variation in fluorescence and therefore a reliable tracer dye. This is starkly illustrated by comparing in FIG. 6 how an unencapsulated dye like RWT has large variations in fluorescence but in FIG. 10 an encapsulated dye like RB does not significantly vary.

In at least one embodiment the encapsulated tracer is used to monitor and/or control the dosage of a treatment chemical added to a process system. Representative monitoring/controlling systems include online and in real time controls such as using TRASAR or 3D TRASAR technology, or similar technology, which satisfy a long-felt but unmet need in the industry. In at least one embodiment the addition of the treatment chemical is an automated process in which a diagnostic method is used to determine that a particular amount of chemical must be added to the system, the chemical is then added and the feed of the chemical ceases when the measured fluorescence of the encapsulated tracer indicates that the correct amount of chemical has been added.

The ability to automate such treatment can improve the efficiency and reduce total cost of operation of raw water and/or industrial wastewater treatment systems, meeting the industry's need. The invention at hand can be used to improve effluent quality for regulatory compliance and system stability. The invention can also allow for more accurate chemical dosing for performance optimization and alarms on system issues, such as pump failures and empty chemical tanks, thereby reducing system upsets. The invention can be used in any and all of the various wastewater treatments, stages and/or automation processes, such as automation of dissolved air flotation ("DAF") and clarifier.

A wastewater treatment plant can take on various embodiments. The plant will typically comprise various treatment stages in sequence: primary treatment; secondary treatment; tertiary treatment; sludge stabilization; sludge thickening; and sludge dewatering. An industrial wastewater treatment plant can have some or all of the stages of the typical wastewater treatment plant.

In primary treatment, a screen is firstly used to remove large debris and particles, and a dissolved air flotation ("DAF") device or clarifier is then used to separate suspended solids. Treatment chemicals, such as coagulant, flocculant, and possibly heavy metal removing reagents, are usually added to treat primary wastewater.

In secondary treatment, aerobic or anaerobic biological systems are used to remove dissolved solids and contaminants. Treatment chemicals, such as coagulant, flocculant, or membrane flux enhancers, are added in the effluent of biological systems to separate the solids generated by the biological systems. After chemical addition, a clarifier, a DAF, a membrane, a filter system, or some combination of one or more of these is used to separate the solids generated in the secondary treatment.

Following secondary treatment, tertiary treatment includes chemical oxidation of persistent contaminants or adsorption of pollutants using sorbents like activated carbon. Treatment chemicals used in tertiary treatment include oxidants, such as hydrogen peroxide. The final effluent after tertiary treatment is either discharged to surface water or recycled back to plant processes.

The sludge (solids) separated in primary treatment and secondary treatment is combined for further treatments to remove residual water from solids. Sludge stabilization using anaerobic digesters and sludge thickening are the pretreatment steps before sludge dewatering. In sludge dewatering, flocculant (coagulant as well in some cases) can be added before the sludge is sent to a sludge dewatering device, such as a belt press or centrifuge.

In at least one embodiment, the encapsulated tracer dye is one that has a maximal fluorescent emission wavelength higher than 550 nm. In at least one embodiment the dye is one including derivatives of xanthene, oxazine, cyanine, styryl, coumarin, porphin, nanocrystal, perylene, phthalocyanine, and any combinations thereof. In group of xanthene dye derivatives of, it includes Rhodamine WT, Sulforhodamine B, Rhodamine B, and any combinations thereof.

In at least one embodiment, the method is performed automatically via feedback control. A preferred embodiment incorporates TRASAR or 3D TRASAR technology, available from Nalco, an Ecolab Company, 1601 West Diehl Road, Naperville, Ill. 60563, www.nalco.com. In at least one embodiment the encapsulated dye is fed alongside a non-encapsulated dye and/or alongside a dye tagged treatment chemical. In at least one embodiment the effectiveness of the use of any one of these dyes is measured by comparing its fluorescence to that of a co-present encapsulated dye, inert dye, and/or dye tagged treatment chemical.

In at least one embodiment, the encapsulated dye is essentially, substantially, and/or effectively inert with respect to fluorescence, optical properties, spectrometric properties, and/or chemical reactivity with any material in the liquid it is introduced to and/or the treatment chemical it is co-present with.

In at least one embodiment, the treatment chemical may comprise a coagulant, a flocculant, both a coagulant and a flocculant, or some combination of multiple coagulants and/or flocculants.

In at least one embodiment, the method may additionally comprise the step of measuring turbidity of the industrial wastewater and/or raw water. If so, then the method may additionally comprise the step of correcting the measuring the fluorescence for the measured turbidity. The method may additionally comprise the step of adjusting the dosing based on the corrected measured fluorescence.

A representative example of encapsulation (which refers to it as "microencapsulation") is described in scientific article *Microencapsulation: A Review*, by Jyothi Sri S., et al., International Journal of Pharma and Bio Sciences, Vol. 3 Issue 1 (2012) (hereinafter "Micro-Article"). In at least one embodiment the tracer dye is encapsulated using at least one method/technology, described in Micro-Article. In at least one embodiment the capsule has at least one shape, structure, morphology, and/or at least one property as at least one microcapsule described in Micro-Article. In at least one embodiment the tracer dye is encapsulated using at least one of the methods: solvent evaporation, polymer-polymer incompatibility, hydrogel microspheres, thermal gelation, gelation, interfacial polycondensation, polymerization, spray drying, spray-congealing, pan coating, fluidized bed, droplet freezing, droplet gelation, extrusion, centrifugal extrusion, spinning disk, supercritical fluid, coacervation, and any combination thereof. In at least one embodiment the capsules may be one or more of: microcapsules, nanocapsules, microspheres, microparticles, nanospheres, nanoparticles, liposomes, niosomes, and any combination thereof.

In at least one embodiment, the encapsulation is accomplished by positioning a mass of the tracer dye within a capsule comprising at least one surfactant. In at least one embodiment the positioning is accomplished by mixing powder forms of surfactant(s) and tracer dye, melting the mixture, cooling the melt so a solid mixture forms, and dissolving the solid mixture in a liquid (including but not limited to water). In at least one embodiment the positioning is accomplished by dissolving the surfactant in a liquid (including but not limited to water) to form the capsule first, and then dissolving the dye into the capsule solution.

In at least one embodiment the ratio of tracer dye to surfactant (or treatment chemical) (by weight) is from 0.01:50 to 2:1 (tracer dye:surfactant/treatment chemical) with preferable ranges of 1:20 to 3:10. In many cases, if the ratio of tracer dye to surfactant/treatment chemical is not correct for the specific surfactant, treatment chemical, of process system present, the tracer dye will not remain within the capsule, as a result, in at least one embodiment the ratio is dosed to afford a stable capsule that would not be stable but for the correct ratio.

In at least one embodiment the surfactant(s) may be anionic, cationic, non-ionic, zwitterionic, amphoteric, and any combination thereof.

In at least one embodiment the surfactant is a multiblock co polymer. In a multiblock copolymer the polymer chain comprises a discrete first region made up of a first series of one or more regularly repeating structural units and then at least one other region made up of a different series of one or more regularly repeating structural units. Thus it is understood that a di-block copolymer has two distinct regions, a tri-block has three distinct regions and so forth. In at least one embodiment at least one region (of a polymer having only one or more than one regions) comprises regularly repeating structural units made from PEO (polyethylene oxide) monomers. In at least one embodiment at least one region (of a polymer having only one or more than one regions) comprises regularly repeating structural units made from PPO (polypropylene oxide-polyethylene oxide) monomers. In at least one embodiment the surfactant(s) is a PEO-PPO-PEO tri-block copolymer.

In at least one embodiment the encapsulated tracer is used to measure the amount of treatment chemical added to a process liquid including but not limited to boiler water, cooling water, raw water, wastewater, papermaking process water or wastewater, food processing process water or wastewater, oil refining process water or wastewater, oil extraction process water or wastewater, hydraulic fracturing fluid process water or wastewater, chemical synthesis process water or wastewater, manufacturing process water or wastewater, industrial process water or wastewater, sewage treatment water, laundry water, and mining process water or wastewater.

A person of ordinary skill in the art will appreciate that the above disclosure can also be accomplished using a method of spectrometry other than or in addition to fluorescence. As such the above disclosure can also be applied substituting fluorescence with one or more other forms of spectrometry mutandis mutandis. In at least one embodiment the encapsulated material added to a treatment chemical is a material subject to analysis by spectrometry and its spectrometry properties are substantially unaffected when it contacts either the treatment chemical or a process liquid because of the encapsulation.

In at least one embodiment the encapsulated material displays at least one form of spectrometry properties when encapsulated and a different one when not encapsulated and the measuring device is calibrated to account for the spectrometry properties when encapsulated. For example if a given mass of tracer dye fluoresces at a particular wavelength or intensity when un-encapsulated and fluoresces at a particular wavelength or intensity when encapsulated, the fluorescence measuring device is calibrated to calculate the amount of treatment chemical present based on the wavelength or intensity when encapsulated.

Without being limited by a particular theory or design of the invention or of the scope afforded in construing the claims, it is believed that in certain environments when the pH of the environment exceeds the pKa of the tracer dye, carbonyl groups on the tracer dye form $COO^-$ groups which become highly reactive with positively charged ions such as the aluminum/inorganic coagulants. Because encapsulation prevents contact between these items and the carbonyl groups it renders inert tracers that would otherwise be reactive.

EXAMPLES

The foregoing may be better understood by reference to the following examples, which are presented for purposes of illustration and are not intended to limit the scope of the invention. In particular the examples demonstrate representative examples of principles innate to the invention and these principles are not strictly limited to the specific condition recited in these examples. As a result it should be understood that the invention encompasses various changes and modifications to the examples described herein and such changes and modifications can be made without departing from the spirit and scope of the invention and without diminishing its intended advantages. It is therefore intended that such changes and modifications be covered by the appended claims.

Example 1

Wastewater screening tests were conducted using both real wastewater and synthetic wastewater contaminant solution. Real wastewater samples were collected from different industries such as paper, oil refinery and manufacturing. Synthetic wastewater contaminant solution was prepared by adding different contaminants into DI (deionized) water. The contaminants included hardness, surfactants, oils and fine particles. 50 ppb or 100 ppb dye was added into these wastewater samples or wastewater contaminant samples and the fluorescence was measured. The measured fluorescence was then normalized by the fluorescence of dye in DI water at the same concentration. The normalized fluorescence was termed as variation in the graphs. If wastewater or wastewater contaminant does not interfere with the fluorescence, the variation is 100%, otherwise, variation is significantly higher or lower than 100%.

Figure 1:
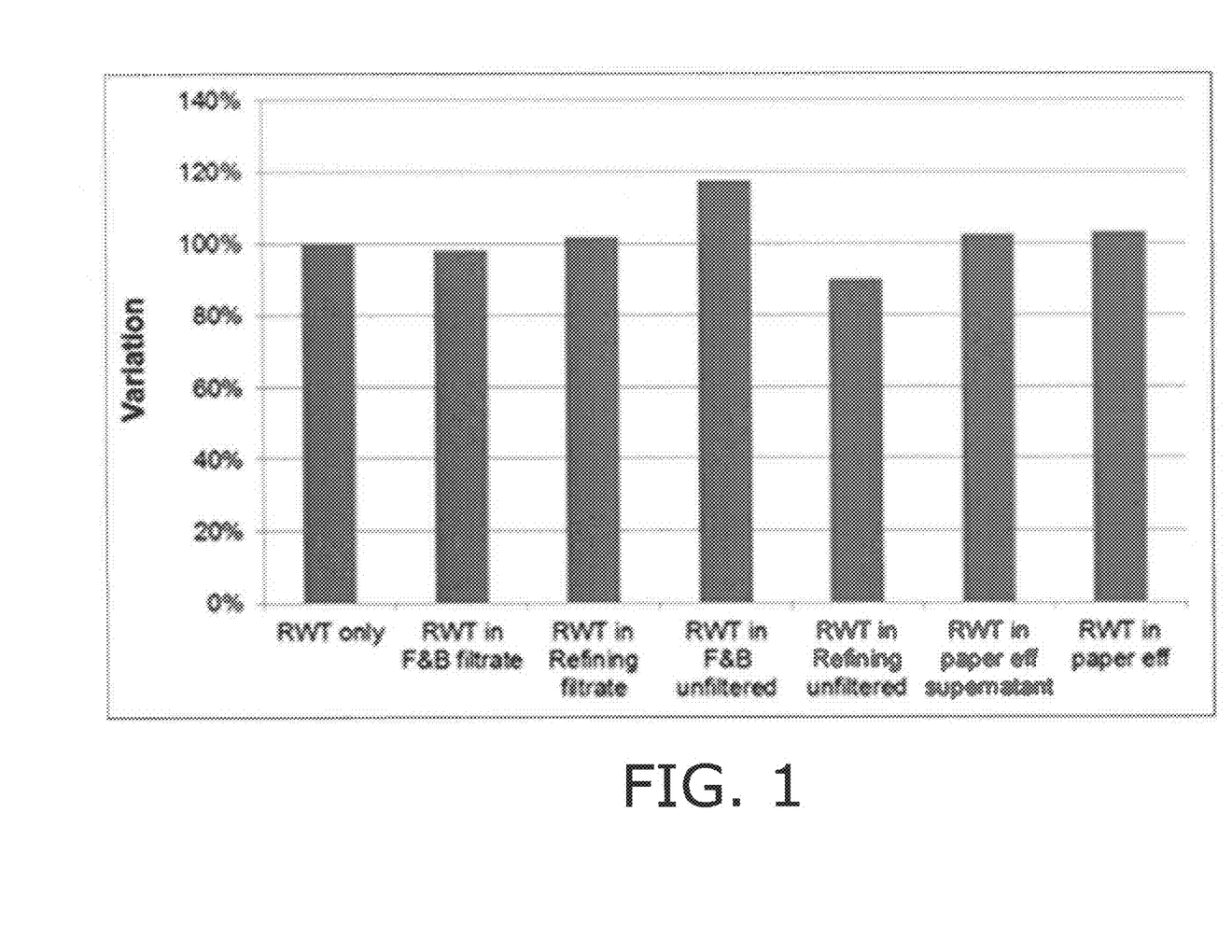
FIG. 1 is a graph illustrating RWT dye's fluorescence variations when placed in wastewaters from different industries, 100% indicates no variation in fluorescence, deviations from 100% indicate inconsistent changes in fluorescence, and 0% indicates virtually no consistency in fluorescence.
Figure 2:
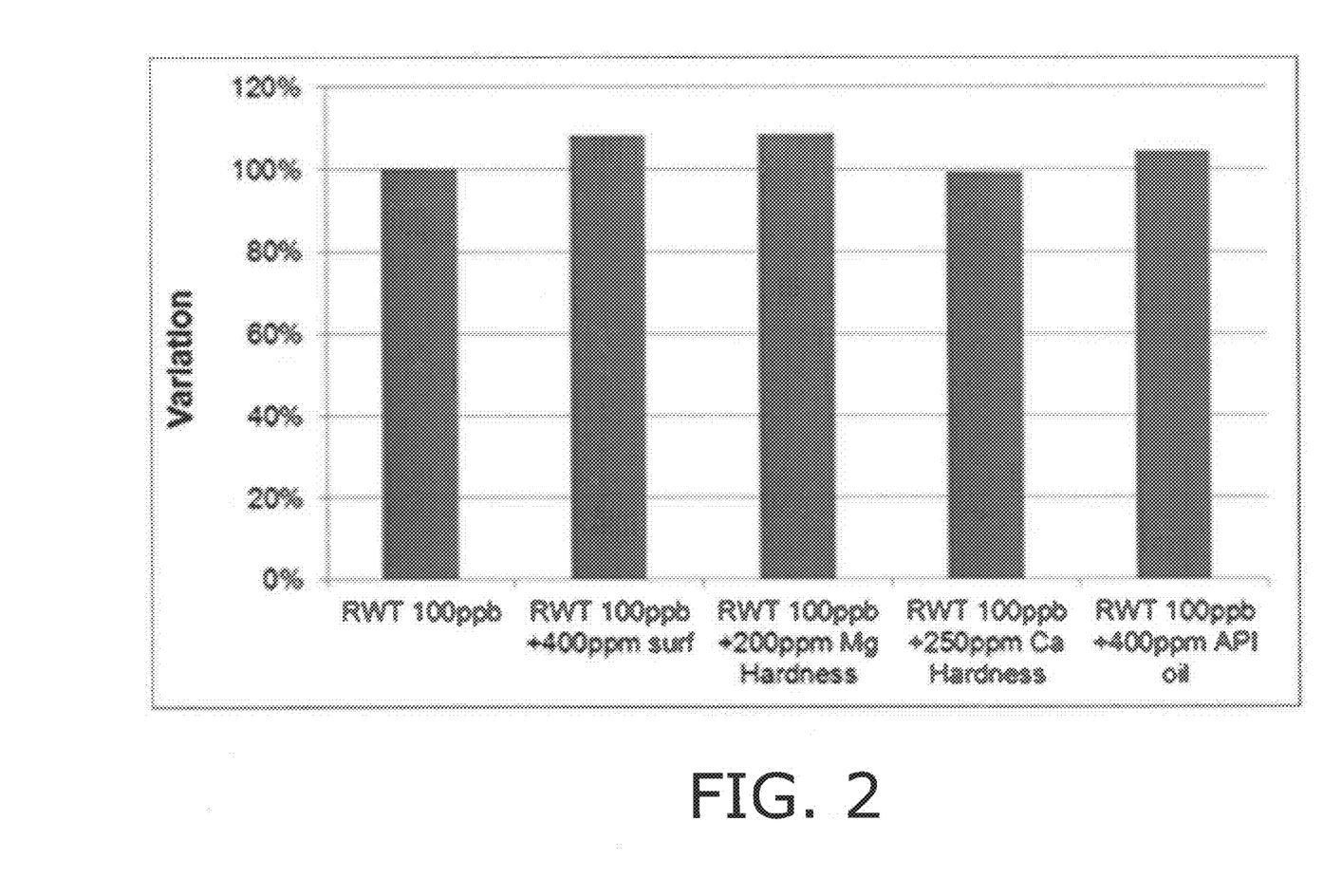
FIG. 2 is a graph illustrating RWT dye's fluorescence variations when in contact with different kinds of wastewater contaminants.

Among all the dyes tested, Rhodamine WT (RWT) and Sulforhodamine (SRB) passed these screening tests. FIGS. 1 and 2 show the screening results for RWT, where there was very minimal interference by various wastewater samples from target industries (FIG. 1) and various contaminants, e.g. oil, hardness, surfactants, and fine particles (FIG. 2). On the other hand, most of dyes we studied failed to pass such tests. As an example, the screening tests for Rohodamine B (RB) were shown in FIGS. 3 and 4, where significant interference was seen from various wastewater samples or typical contaminants such as oils and surfactants.

Example 2

This example tested the compatibility of dye with typical wastewater treatment chemicals. Dye was added into pure product to make the final dye concentration of 0.1% (w/w), and the fluorescence of the solution is recorded over time. As shown in FIG. 3, SRB was not compatible with most of the typical wastewater treatment products and failed in the compatibility test.

The other aspect of compatibility test was to see if the fluorescence-pH dependency of the dye is changed by the presence of wastewater treatment product. 100 ppb dye solution was prepared in DI water with or without 100 ppm wastewater product. The fluorescence of the solution was then measured after the pH of the solution was adjusted to desired values. As shown in FIG. 2, the dependence of the fluorescence of RWT in inorganic aluminum based coagulant and a mixture of organic coagulant with inorganic aluminum based coagulant on pH was significantly different from the one of pure RWT solution, indicating there were some interactions between RWT and inorganic aluminum based coagulant or a mixture of organic coagulant with inorganic aluminum based coagulant when pH is below 6.

Based on the screening tests described in both example 1 and 2, none of the dyes we studied meets the requirements for being inert dye.

Example 3

Encapsulated RB was prepared as follows: powders of surfactant (Pluronics (F-127 or F-108 manufactured by BASF) and Rhodamine B were first mixed at different mass ratios (1:3 to 1:10), then heated up to ~80 C until all the powders melted. The melted mass was then cooled down which became solid. 0.1% (w/w) encapsulated RB solution in DI or in wastewater treatment products was prepared by adding desired amount of Pluronic/RB solid into DI water or pure wastewater treatment product under stirring until all the solids dissolve.

Example 4

Figure 5:
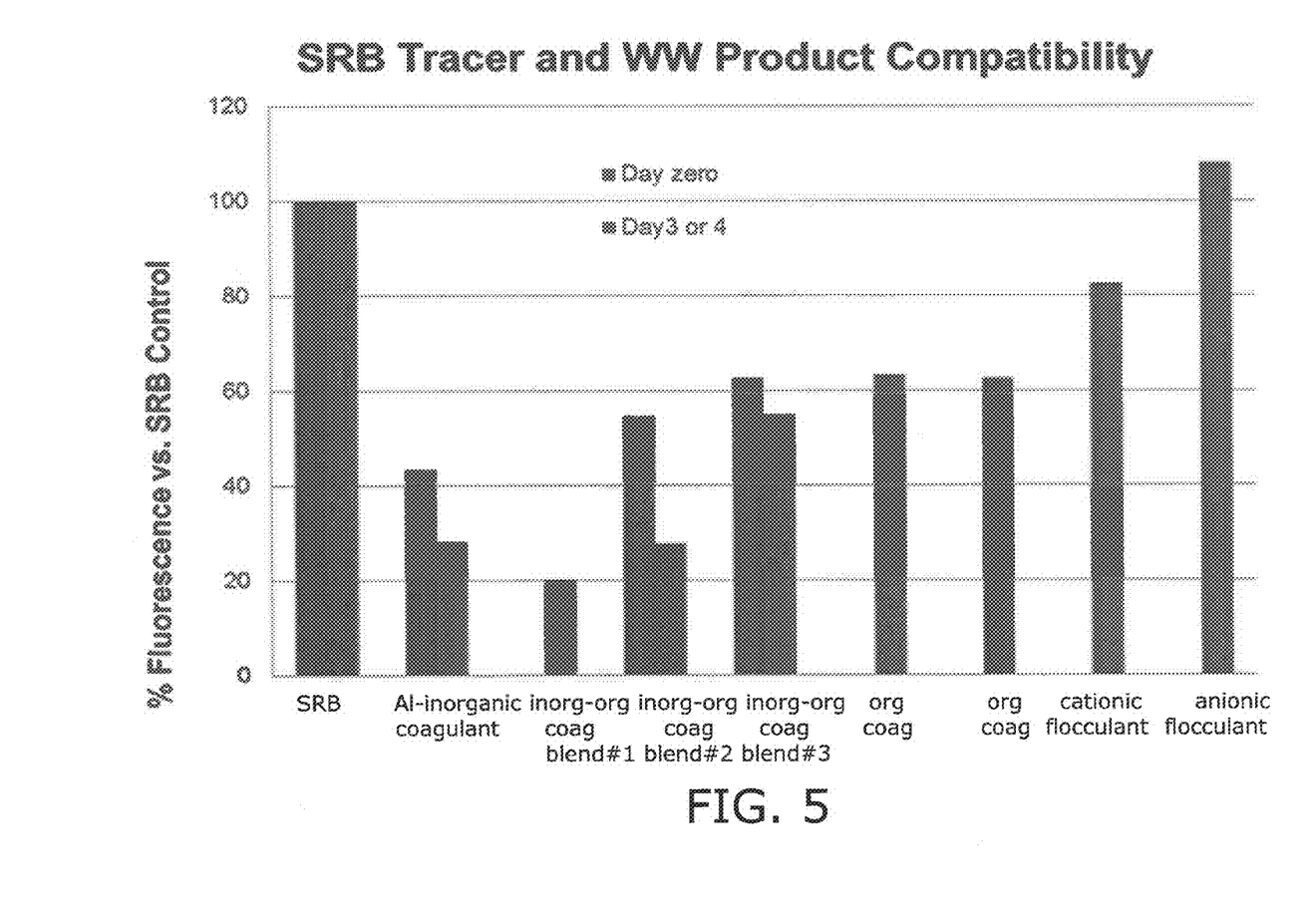
FIG. 5 is a graph illustrating how wastewater treatment chemicals cause fluorescence variations in SRB dye.

Encapsulated RB was tested using the same procedure described in example 1 and 2. As shown in FIGS. 5 and 6, fluorescence of encapsulated RB was not significantly interfered with by various wastewaters from different industries and various wastewater contaminants. The traced wastewater treatment products by encapsulated RB were found to be stable at room temperature and 50° C. for at least 2 and half months. The traced product was also stable after three cycles of freeze and thaw, as shown in FIG. 5. Furthermore, the pH dependence of encapsulated RB fluorescence with wastewater treatment product was same as that of pure Encapsulated RB solution, as shown in FIG. 6.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range. All percentages, ratios and proportions herein are by weight unless otherwise specified.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of treating wastewater comprising introducing into wastewater (a) an aluminum salt and (b) an encapsulated tracer comprising a capsule encapsulating a core, the core comprising a xanthene derivative selected from Rhodamine WT and Rhodamine B, and the capsule comprising a polyethhylene oxide-polypropylene oxide-polyethylene oxide ("PEO-PPO-PEO") tri-block copolymer, the encapsulated tracer introduced into the wastewater in a dosage such that the amount of aluminum salt introduced to the wastewater can be determined from fluorescence of the xanthene derivative present in the encapsulated tracer, wherein the xanthene derivative and the PEO-PPO-PEO tri-block copolymer are present in the encapsulated tracer at a ratio of from 1:20 to 3:10 by weight, and the wastewater has a pH of 6 or less.

2. The method of claim 1, wherein the wastewater has a pH of from about 2 to 6.

3. The method of claim 1, wherein the wastewater has a pH of from about 3 to 6.

4. The method of claim 1, further comprising introducing into wastewater an iron salt.

5. The method of claim 4, wherein the iron salt comprises ferric chloride, ferric sulfate, or a combination thereof.

6. The method of claim 1, wherein the aluminum salt comprises aluminum sulfate, aluminum chloride, polyaluminum chloride, aluminum chloride hydrate, or a combination thereof.

7. The method of claim 1, wherein the aluminum salt is polyaluminum chloride.

8. The method of claim 1, wherein the inorganic coagulant and the encapsulated tracer are introduced into the wastewater at a primary treatment stage.

9. The method of claim 1, wherein the inorganic coagulant and the encapsulated tracer are introduced into the wastewater at a secondary treatment stage.

10. The method of claim 1, further comprising measuring fluorometric properties of the xanthene derivative and correlating the measured fluorometric properties with an amount of inorganic coagulant present in the wastewater.

11. The method of claim 1, wherein the core further comprises a derivative of oxazine, cyanine, styryl, coumarin, porphin, nanocrystal, perylene, phthalocyanine, or a combination thereof.

12. The method of claim 1, wherein the xanthene derivative is selected from rhodamine WT, sulforhodamine B, rhodamine B, or a combination thereof.

13. The method of claim 1, wherein the inorganic coagulant and the encapsulated tracer are introduced into the wastewater as a liquid treatment chemical.

14. The method of claim 13, wherein the liquid treatment chemical further comprises an agent selected from a flocculant, an anti-scaling agent, an anti-corrosion agent, a biocide, an oxygen scavenger, a hardness removal agent, or a combination thereof.

15. The method of claim 13, wherein the liquid treatment chemical further comprises a flocculant.

16. The method of claim 13, wherein the liquid treatment chemical further comprises an organic coagulant.

17. The method of claim 16, wherein the organic coagulant is selected from a polyamine, a polyquaternary, polydiallyldimethylammonium chloride ("polyDADMAC"), epichlorohydrin-dimethylamine ("Epi-DMA"), or a combination thereof.

* * * * *

UNITED STATES PATENT AND TRADEMARK OFFICE
CERTIFICATE OF CORRECTION

PATENT NO. : 10,139,385 B2
APPLICATION NO. : 13/964478
DATED : November 27, 2018
INVENTOR(S) : Lan Xiao et al.

Page 1 of 1

It is certified that error appears in the above-identified patent and that said Letters Patent is hereby corrected as shown below:

In the Claims

At Column 12, Line 15, please delete "polyethhylene" and insert --polyethylene--

At Column 13, Line 2, please delete "polyquatemary" and insert --polyquaternary--

Signed and Sealed this
Twenty-sixth Day of February, 2019

Andrei Iancu
*Director of the United States Patent and Trademark Office*